(12) United States Patent
Kitano et al.

(10) Patent No.: US 7,974,382 B2
(45) Date of Patent: Jul. 5, 2011

(54) RADIOGRAPHIC IMAGING SYSTEM, RADIOGRAPHIC IMAGING DEVICE, CONTROL DEVICE, AND RADIOGRAPHIC IMAGING CONTROL METHOD

(75) Inventors: Kouichi Kitano, Kanagawa (JP); Keiji Tsubota, Kanagawa (JP); Yutaka Yoshida, Kanagawa (JP); Fumito Nariyuki, Kanagawa (JP); Yasunori Ohta, Kanagawa (JP); Naoyuki Nishino, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 141 days.

(21) Appl. No.: 12/540,370

(22) Filed: Aug. 13, 2009

(65) Prior Publication Data
US 2010/0054406 A1    Mar. 4, 2010

(30) Foreign Application Priority Data

Aug. 28, 2008 (JP) .................................. 2008-219935
Mar. 30, 2009 (JP) .................................. 2009-081992

(51) Int. Cl.
*H05G 1/56* (2006.01)

(52) U.S. Cl. ........................................ 378/114; 378/62

(58) Field of Classification Search .................... 378/62, 378/114–117
See application file for complete search history.

(56) References Cited

FOREIGN PATENT DOCUMENTS

JP    2008-132216 A    6/2008

*Primary Examiner* — Courtney Thomas
(74) *Attorney, Agent, or Firm* — Solaris Intellectual Property Group, PLLC

(57) ABSTRACT

There is provided a radiographic imaging system including: a radiographic imaging device including a generating section that captures a radiographic image expressed by irradiated radiation and generates image information expressing the captured radiographic image, and a first communication section that transmits, plural times and by wireless communication and even during a response wait time period, imaging start instructing information that instructs starting of imaging when preparations for capturing a radiographic image by the generating section have been completed; and a control device having a second communication section that can communicate by wireless communication with the first communication section, and a control section that controls a radiation irradiating section such that radiation is irradiated with respect to the radiographic imaging device in a case in which the second communication section receives any of the imaging start instructing information that are transmitted plural times from the first communication section.

18 Claims, 11 Drawing Sheets

RADIOGRAPHIC IMAGING SYSTEM, RADIOGRAPHIC IMAGING DEVICE, CONTROL DEVICE, AND RADIOGRAPHIC IMAGING CONTROL METHOD

CROSS-REFERENCE TO RELATED APPLICATIONS

This application is based on and claims priority under 35 USC 119 from Japanese Patent Applications No. 2008-219935 filed on Aug. 28, 2008 and No. 2009-081992 filed on Mar. 30, 2009, the disclosures of which are incorporated by reference herein.

BACKGROUND

1. Technical Field

The present invention relates to a radiographic imaging system, a radiographic imaging device, a control device, and a radiographic imaging control method.

2. Related Art

FPDs (Flat Panel Detectors), in which a radiation-sensitive layer is disposed on a TFT (Thin Film Transistor) active matrix substrate and that can convert radiation directly into digital data, have been put into practice in recent years. Portable radiographic imaging devices (hereinafter also called "electronic cassettes"), that generate image information expressing a radiographic image manifested by radiation irradiated by using an FPD or the like and that store the generated image information, have been put into practice in recent years.

Because the electronic cassette is portable, a patient can be captured a radiographic image as is while on a stretcher or bed, and the place to be imaged can be adjusted by changing the position of the electronic cassette. Therefore, even patients who cannot move can be dealt with flexibly.

At an FPD, even in a state in which X-rays are not being irradiated, charges are generated due to dark current or the like, and the charges are accumulated in the respective pixels. Therefore, during standby, the electronic cassette repeatedly carries out a resetting operation of reading-out and deleting the charges accumulated in the respective pixels of the FPD. When instruction information that requests capturing of a radiographic image is received from a control device for control (a so-called console), the electronic cassette transmits to the console instruction information instructing the start of imaging after the resetting operation of one frame has been completed. When the console receives this instruction information, the console causes X-rays to be irradiated from a radiation generating device onto the electronic cassette. After a predetermined time period after transmitting the instruction information, the electronic cassette carries out reading-out of the charges accumulated in the respective pixels of the FPD.

In cases in which the communication between the electronic cassette and the console is wireless communication, there are cases in which the state of the communication becomes unstable and the console receives the instruction information late or cannot receive the instruction information.

Thus, Japanese Patent Application Laid-Open (JP-A) No. 2008-132216 discloses a technique of transitioning from the resetting operation to a charge accumulating state in which charges are accumulated in the respective pixels, not only in cases in which the electronic cassette receives a control signal of the start of irradiation of the X-rays, but also in cases in which the electronic cassette senses the start of irradiation of X-rays from the radiation generating device.

However, in the technique of JP-A No. 2008-132216, even if the start of irradiation of X-rays is sensed during the resetting operation, it is not possible to immediately transition to the charge accumulating state, and the radiation that is irradiated up to the transition to the charge accumulating state is wasted. If the X-ray irradiation time period is lengthened by an amount corresponding thereto, the amount of radiation that the subject is exposed to increases, which is not preferable.

SUMMARY

The present invention was made in view of the above-described circumstances, and an object thereof is to provide a radiographic imaging system, a radiographic imaging device, a control device, and a radiographic imaging control method that can carry out capturing of a radiographic image stably even in cases in which communication between a radiographic imaging device and a control device is wireless communication.

In order to achieve the above-described object, the present invention provides a radiographic imaging system including:

a radiographic imaging device comprising a generating section that captures a radiographic image expressed by irradiated radiation and generates image information expressing the captured radiographic image, and a first communication section that transmits, plural times and by wireless communication and even during a response wait time period, imaging start instructing information that instructs starting of imaging at a time when preparations for capturing a radiographic image by the generating section have been completed; and a control device having a second communication section that is able to communicate by wireless communication with the first communication section, and a control section that controls a radiation irradiating section such that radiation is irradiated with respect to the radiographic imaging device in a case in which the second communication section receives any of the imaging start instructing information that are transmitted plural times from the first communication section.

Namely, in the radiographic imaging device of the first aspect of the present invention, a radiographic image manifested by irradiated radiation is captured by the generating section, and image information expressing the captured radiographic image is generated by the generating section. Imaging start instructing information, that instructs starting of imaging at a time when preparations for capturing a radiographic image by the generating section have been completed, is transmitted by the first communication section plural times and by wireless communication and even during a response wait time period.

On the other hand, at the control device, in a case in which the second communication section, that can communicate with the first communication section by wireless communication, receives any of the imaging start instructing information that are transmitted plural times from the first communication section, the radiation irradiating section is controlled by the control section such that radiation is irradiated with respect to the radiographic imaging device.

In this way, in accordance with the first aspect of the present invention, the radiographic imaging device transmits, plural times and by wireless communication and even during a response wait time period, imaging start instructing information that instructs starting of imaging at a time when preparations for capturing a radiographic image have been completed. In a case in which any of the imaging start instructing information that are transmitted plural times is received, the control device controls the radiation irradiating section such that radiation is irradiated with respect to the radiographic imaging device. Therefore, radiographic images can be captured stably even in cases in which the communication between the radiographic imaging device and the control device is wireless communication.

Note that in the radiographic imaging system of the present invention the first communication section may transmit, at a predetermined cycle, the imaging start instructing information that includes identification information for identifying the number of times of transmissions.

Further, the control section may change a time of causing radiation to be irradiated from the radiation irradiating section, on the basis of the identification information that is included in the imaging start instructing information received at the second communication section.

Moreover, the generating section may have plural charge storing sections that accumulate charges generated by radiation being irradiated, and in which charges are respectively accumulated in accordance with an accumulating time period of the charges, and the first communication section transmits the imaging start instructing information at a time of resetting the charges accumulated in the plural charge storing sections.

Further, the control section may effect control such that, in a case in which the imaging start instructing information is received at the second communication section, reply information is transmitted from the second communication section to the first communication section on the basis of the identification information included in the received imaging start instructing information, and in a case in which the first communication section receives the reply information, the generating section changes a time period for accumulating charges at the charge storing sections at a time of capturing a radiographic image, on the basis of the returned reply information.

Moreover, the control device may further have a receiving section that receives, in two steps, radiographic imaging instructing operations by the generating section, and in at least one case in which an imaging instructing operation of a first step and an imaging instructing operation of a second step are received at the receiving section, the control section transmits, plural times and by wireless communication and even during a response wait time period and from the second communication section, imaging instructing information that corresponds to the step of the imaging instructing operation.

Further, the control device further may have a first notification section that gives notice in a case in which the imaging start instructing information is not received even while standing-by during a predetermined imaging standby time period from transmission of the imaging instructing information that corresponds to the imaging instructing operation of the second step.

Moreover, in a case in which the imaging start instructing information is received at the second communication section, the control section may control the radiation irradiating section, and effect control such that read-out instructing information, that instructs starting of reading-out of accumulated charges, is transmitted from the second communication section to the first communication section after ending of irradiation of radiation from the radiation irradiating section, and in a case in which the first communication section receives the read-out instructing information transmitted from the second communication section, the generating section may start reading-out of the charges accumulated in the charge storing sections.

Further, the control section may transmit the read-out instructing information plural times and by wireless communication and even during a response wait time period, and in a case in which the first communication section receives any of the read-out instructing information that are transmitted plural times from the second communication section, the generating section may start reading-out of the charges accumulated in the charge storing sections.

Moreover, the control section may transmit the read-out instructing information after standing-by for at least a predetermined irradiation standby time period from reception of the imaging start instructing information at the second communication section.

Further, in a case in which the read-out instructing information is not received even if standing-by for a predetermined accumulating standby time period from transmission of the imaging start instructing information plural times, the generating section may start reading-out of the charges accumulated in the charge accumulating sections.

Moreover, the radiographic imaging system of the present invention, the radiographic imaging device may further have a second notification section that gives notice in a case in which the first communication section receives predetermined instruction information relating to capturing of a radiographic image.

Further, the predetermined instruction information may be instruction information requesting capturing of a radiographic image.

Still further, the second notification section may give notice by using at least one of light and sound.

Yet further, the second notification section may be provided at a grasping portion for grasping at a time of carrying a main body of the radiographic imaging device.

On the other hand, a second aspect of the present invention provides a radiographic imaging device of a second aspect of the present invention including:

a generating section that captures a radiographic image expressed by irradiated radiation, and generates image information expressing the captured radiographic image; and a communication section that transmits, plural times and by wireless communication and even during a response wait time period, imaging start instructing information that instructs starting of imaging at a time when preparations for capturing a radiographic image by the generating section have been completed.

Further, a third aspect of the present invention provides a control device including:

a communication section that is able to communicate with a radiographic imaging device that transmits, plural times and by wireless communication and even during a response wait time period, imaging start instructing information that instructs starting of imaging at a time when preparations for capturing a radiographic image have been completed; and a control section that controls a radiation irradiating section such that radiation is irradiated with respect to the radiographic imaging device in a case in which any of the imaging start instructing information that are transmitted plural times is received from the communication section.

Radiographic images can be captured stably by carrying out capturing of the radiographic images by using the radiographic imaging device of the second aspect of the present invention and the control device of the third aspect.

On the other hand, a fourth aspect of the present invention provides a radiographic imaging control method including:

transmitting, plural times and by wireless communication and even during a response wait time period, imaging start instructing information, that instructs starting of imaging at a time when preparations for capturing a radiographic image have been completed, from a radiographic imaging device that captures a radiographic image expressed by irradiated radiation and generates image information expressing the captured radiographic image; and in a case in which any of the imaging start instructing information that are transmitted plural times from the radiographic imaging device is received at a control device that is able to communicate with the radiographic imaging device by wireless communication, controlling, by the control device, a radiation irradiating section such that radiation is irradiated with respect to the radiographic imaging device.

In accordance with the radiographic imaging control method of the fourth aspect of the present invention, because operation is similar to that of the first aspect, radiographic images can be captured stably even in cases in which the communication between the radiographic imaging device and the control device is wireless communication.

In accordance with the present invention, a radiographic imaging device transmits, plural times and by wireless communication and even during a response wait time period, imaging start instructing information that instructs starting of imaging at a time when preparations for capturing a radiographic image have been completed. A control device controls a radiation irradiating section such that radiation is irradiated with respect to the radiographic imaging device in a case in which any of the imaging start instructing information that are transmitted plural times is received. Therefore, the present invention has the effect that radiographic images can be captured stably even in cases in which the communication between the radiographic imaging device and the control device is wireless communication.

BRIEF DESCRIPTION OF THE DRAWINGS

Exemplary embodiments of the present invention will be described in detail based on the following figures, wherein.

DETAILED DESCRIPTION

Hereinafter, preferred embodiments for implementing the present invention will be described in detail with reference to the drawings.

First Exemplary Embodiment

First, the structure of a radiation information system 10 relating to a first exemplary embodiment will be described.

Figure 1:
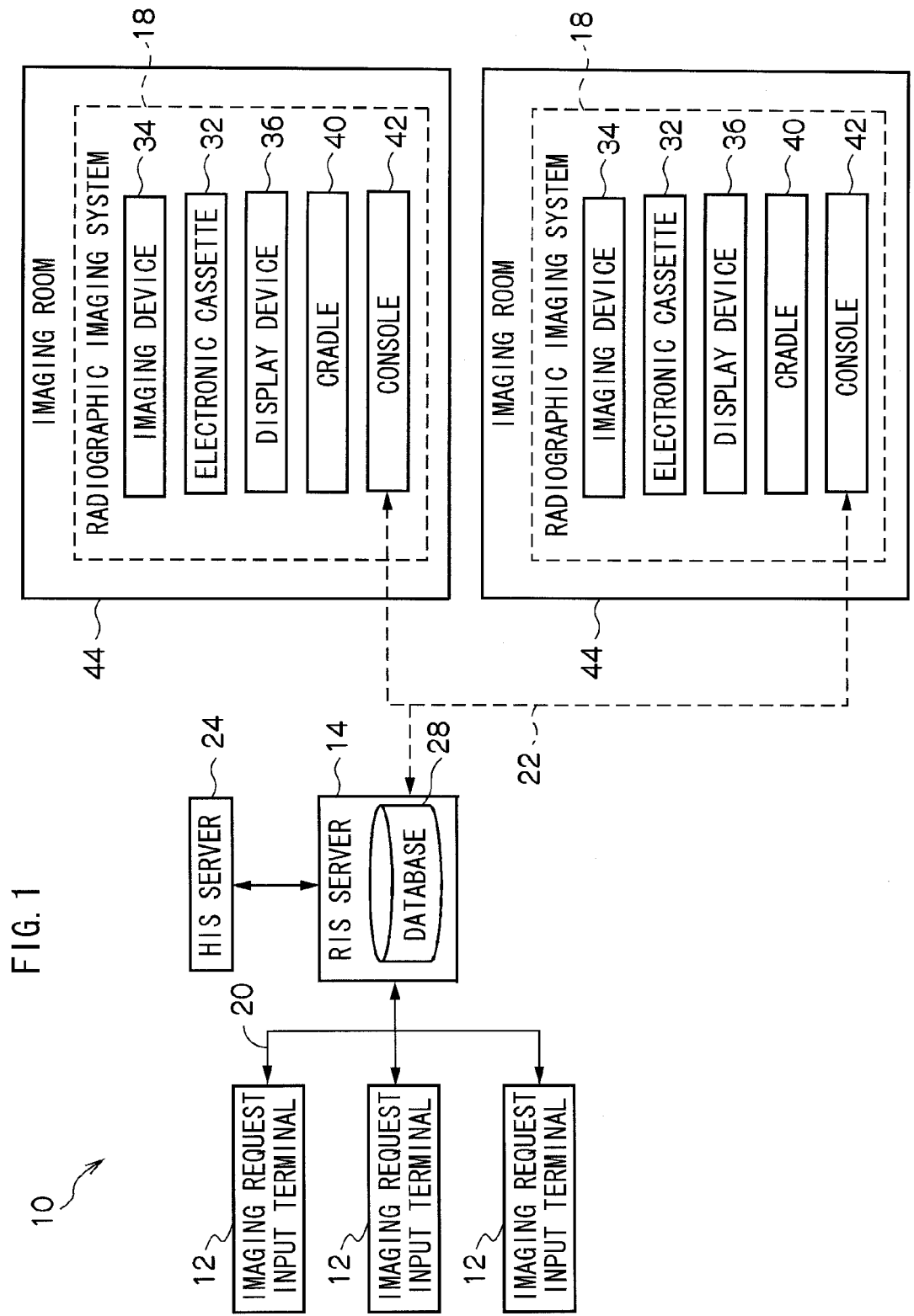
FIG. 1 is a block diagram showing the structure of a radiation information system relating to exemplary embodiments.

A block diagram showing the respective structural elements of the radiation information system 10 (hereinafter also called "RIS 10") relating to the present exemplary embodiment is shown in FIG. 1.

The RIS 10 is a system for carrying out information management such as scheduling of examinations/treatments, recording of diagnoses, and the like in a radiology department, and structures a part of a hospital information system (HIS).

The RIS 10 is structured to include plural imaging request input terminals 12 (hereinafter also called "input terminals 12"), an RIS server 14, and plural radiographic imaging systems 18 (hereinafter also called "imaging systems 18").

The RIS server 14 manages the entire RIS 10, and is structured such that communication between the respective input terminals 12 and the imaging systems 18 is possible by LAN (Local Area Network) cables 20 or a wireless LAN 22. The RIS server 14 is connected to an HIS server 24 that manages the entire HIS.

The input terminal 12 is for a surgeon 26 (see FIG. 2) or a radiology technician to input and browse diagnostic information and reservations of facilities. Requests for capturing of radiographic images (reservations for imaging) are also made from the input terminal 12. Each of the input terminals 12 is structured from a personal computer that is equipped with a display device, and is connected to the RIS 14 by a LAN such that communication therebetween is possible.

The RIS server 14 receives imaging requests from the respective input terminals 12, and manages the radiographic imaging schedule at the imaging systems 18, and is structured to include a database 28.

The database 28 includes: information relating to a patient 30 (see FIG. 2) such as attribute information of the patient 30 (name, sex, birthdate, age, blood type, patient ID, and the like), the patient's history of past illness, history of past examinations/treatments, radiographic images that were taken in the past, and the like; information relating to electronic cassettes 32 of the imaging systems 18 such as the ID number, type, size, sensitivity, regions to be imaged at which the electronic cassette 32 can be used (contents of imaging requests that the electronic cassette 32 can handle), the usage start date, number of times of usage, and the like; and environment information expressing the environments in which radiographic images were captured by using the electronic cassette 32, i.e., environments in which the electronic cassette 32 was used (as an example, an operating room, an imaging room set exclusively for the capturing of radiographic images, or the like).

The imaging system 18 carries out capturing of radiographic images by operation of the surgeon 26 or a radiology technician in accordance with instructions from the RIS server 14. The imaging system 18 includes: a imaging device 34 that irradiates, onto a subject of imaging, radiation X formed of a radiation amount conforming to imaging conditions; the electronic cassette 32 that incorporates therein a radiation detector 60 (see FIG. 3) that detects the radiation X that has been transmitted through the patient 30 and that converts the detected radiation into radiographic image information; a display device 36 that displays a radiographic image that is based on the radiation X detected by the radiation detector 60; a cradle 40 that charges a battery incorporated in the electronic cassette 32; and a console 42 that controls the electronic cassette 32, the imaging device 34, the display device 36 and the cradle 40.

Figure 2:
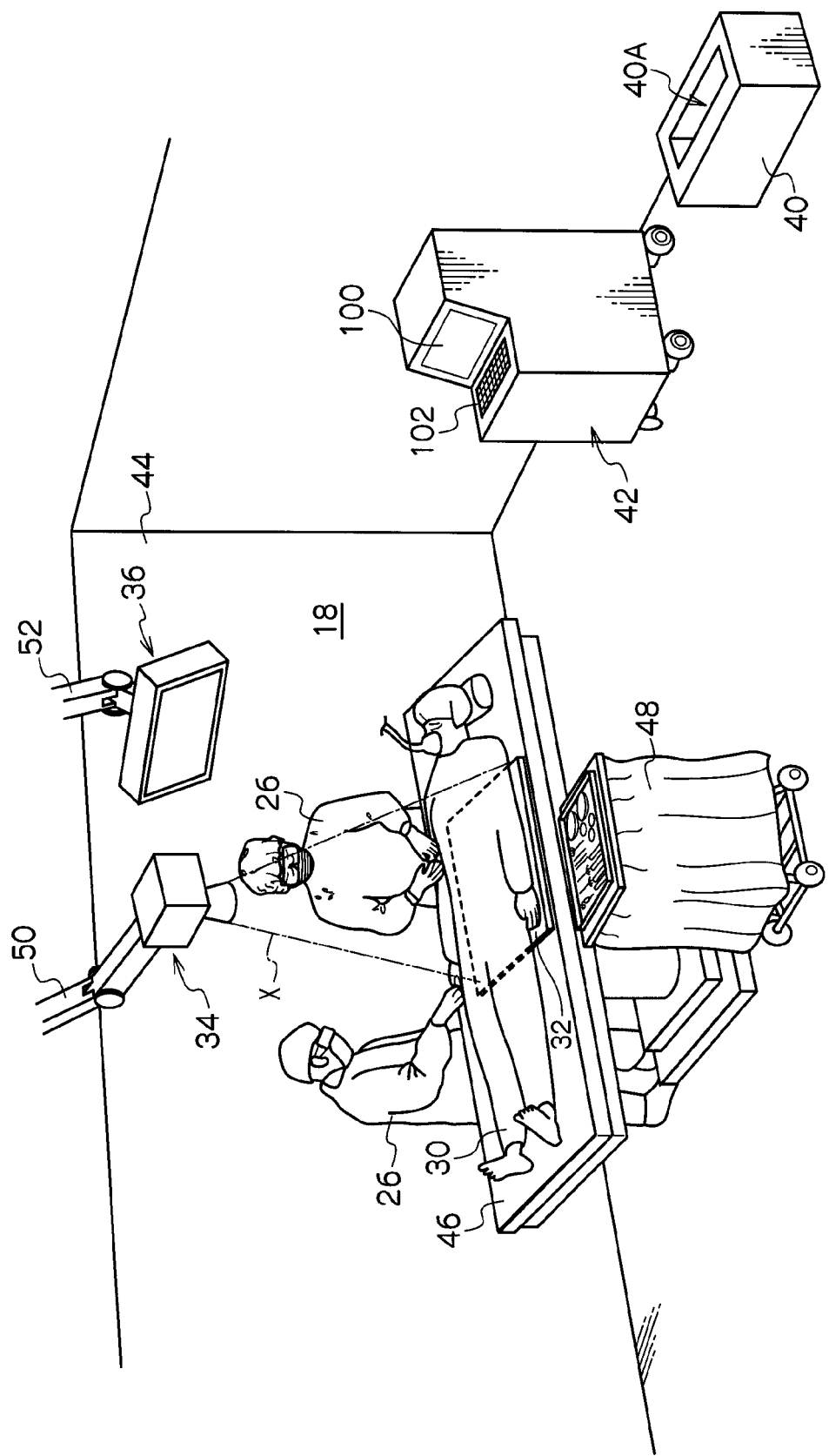
FIG. 2 is a drawing showing the situation in an operating room in which a radiographic imaging system relating to the exemplary embodiments is set.

A situation, in which the imaging system 18 is set in an operating room 44 that serves as an imaging room, is illustrated in FIG. 2 as an example of a situation in which the imaging system 18 relating to the present exemplary embodiment is disposed. In the imaging system 18 relating to the present exemplary embodiment, the imaging device 34 and the display device 36, and the console 42 are respectively connected by cables, and transmission and reception of various types of information is carried out by wired communication. The cables that connect the respective devices are omitted from FIG. 2. Further, the transmission and reception of various types of information between the electronic cassette 32 and the console 42 are carried out by wireless communication.

In the operating room 44 of FIG. 2, in addition to the imaging system 18, an operating table 46 on which the patient 30 lays is provided, and an instrument table 48, on which various types of instruments that the surgeon 26 uses in surgery are placed, is disposed at the side of the operating table 46. Various devices that are needed in surgery such as anesthesia equipment, suction equipment, an electrocardiograph, a blood pressure meter, and the like are disposed around the operating table 46 (these devices are omitted from FIG. 2).

The imaging device 34 is connected to a universal arm 50, and can be moved to a desired position that corresponds to the region to be image captured of the patient 30, and can be withdrawn to a position at which it does not get in the way of the surgery performed by the surgeon 26. Similarly, the display device 36 is connected to a universal arm 52, and can be moved to a position at which the surgeon 26 can easily confirm the captured radiographic image.

An accommodating portion 40A, in which the electronic cassette 32 can be accommodated, is formed in the cradle 40.

At times of standby, the electronic cassette 32 is stored in the accommodating portion 40A of the cradle 40, and the battery incorporated in the electronic cassette 32 is charged. At times of capturing radiographic images, the electronic cassette 32 is taken-out from the cradle 40 and is disposed at the region to be imaged of the patient 30.

Note that the electronic cassette 32 is not limited to cases of being used in the operating room 44, and for example, can be used in medical examinations or in doctors' rounds within a hospital as well.

Figure 3:
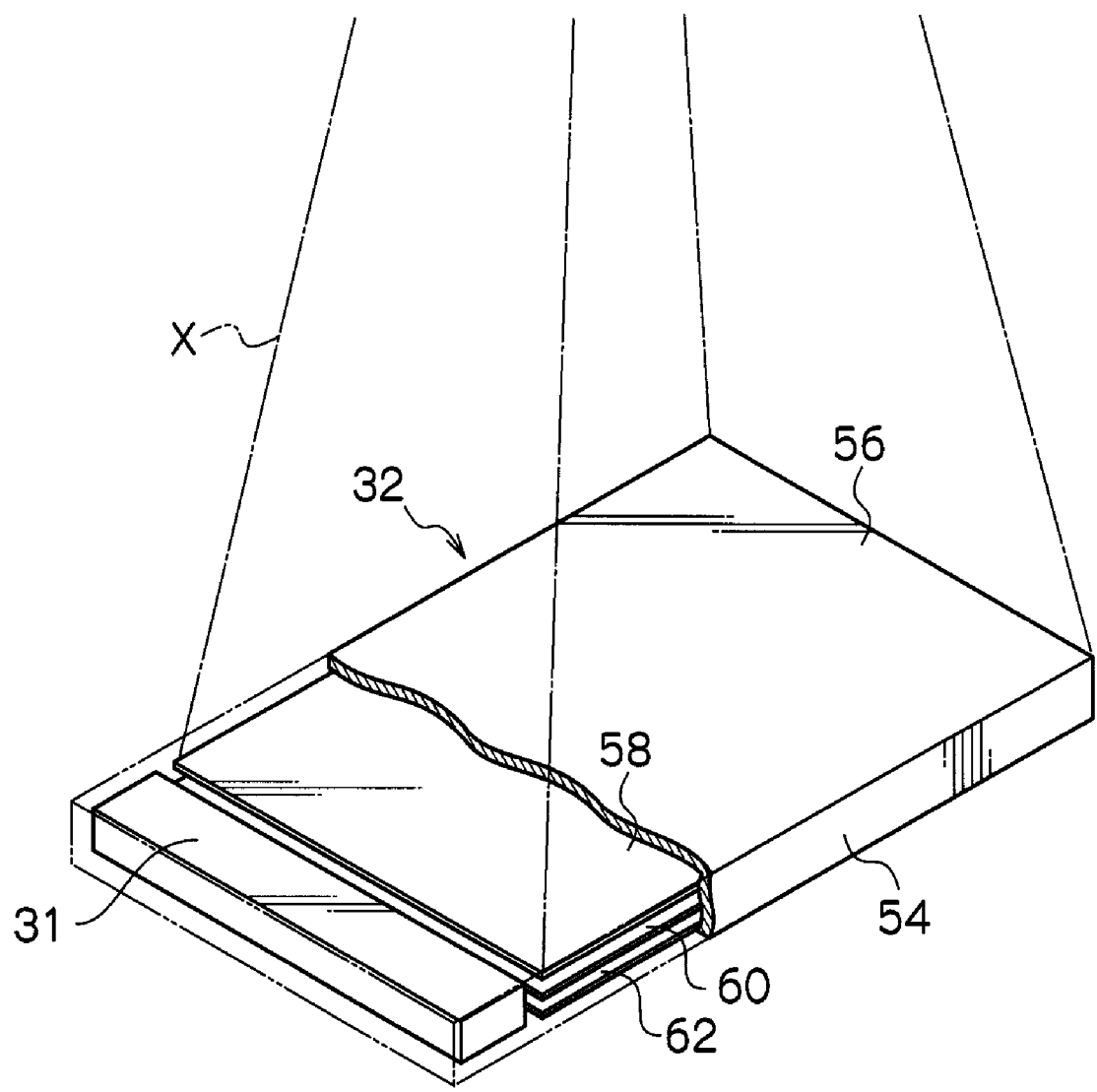
FIG. 3 is a transparent perspective view showing the internal structure of an electronic cassette relating to the exemplary embodiments.

The internal structure of the electronic cassette 32 relating to the first exemplary embodiment is shown in FIG. 3.

Figure 4:
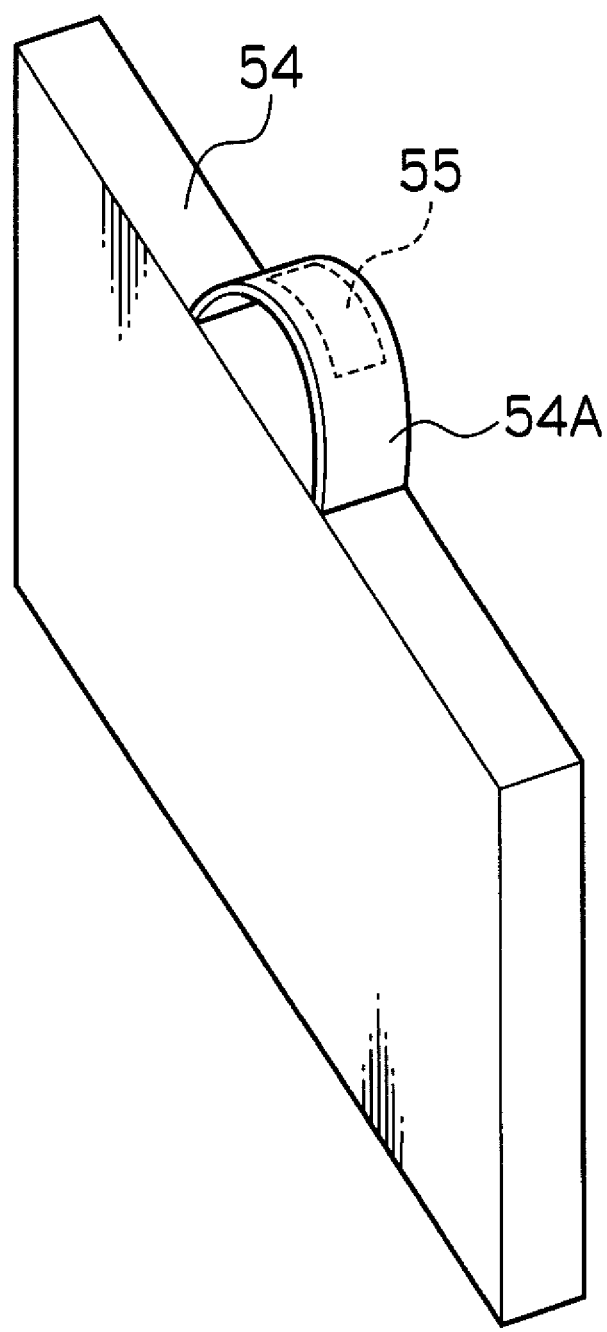
FIG. 4 is a perspective view showing the structure of the electronic cassette relating to the exemplary embodiments.

As shown in FIG. 3, the electronic cassette 32 has a housing 54 formed from a material through which the radiation X is transmitted, and is a structure that is waterproof and airtight. When the electronic cassette 32 is being used in the operating room 44 or the like, there is the concern that blood or other various germs will adhere thereto. Thus, by making the electronic cassette 32 be a waterproof and airtight structure and disinfectingly cleaning it as needed, one electronic cassette 32 can be used repeatedly in continuation. As shown in FIG. 4, a handle 54A is provided at the housing 54 so as to make grasping easy at the time of carrying the electronic cassette 32. A light-emitting portion 55 is provided at the surface of the handle 54A.

A grid 58 that removes the scattered radiation of the radiation X due to the patient 30, the radiation detector 60 that detects the radiation X that has been transmitted through the patient 30, and a lead plate 62 that absorbs the back-scattered radiation of the radiation X, are disposed within the housing 54 (see FIG. 3) in that order from an irradiation surface 56 side of the housing 54 on which the radiation X is irradiated. Note that the irradiation surface 56 of the housing 54 may be structured as the grid 58.

A case 31, that accommodates a secondary battery that can be charged and electronic circuits including a microcomputer, is disposed at one end side of the interior of the housing 54. The radiation detector 60 and the electronic circuits are operated by electric power that is supplied from the secondary battery disposed in the case 31. In order to avoid damage, that accompanies the irradiation of the radiation X, to the various types of circuits that are accommodated within the case 31, it is preferable to dispose a lead plate or the like at an irradiation surface 22 side of the case 31.

Figure 5:
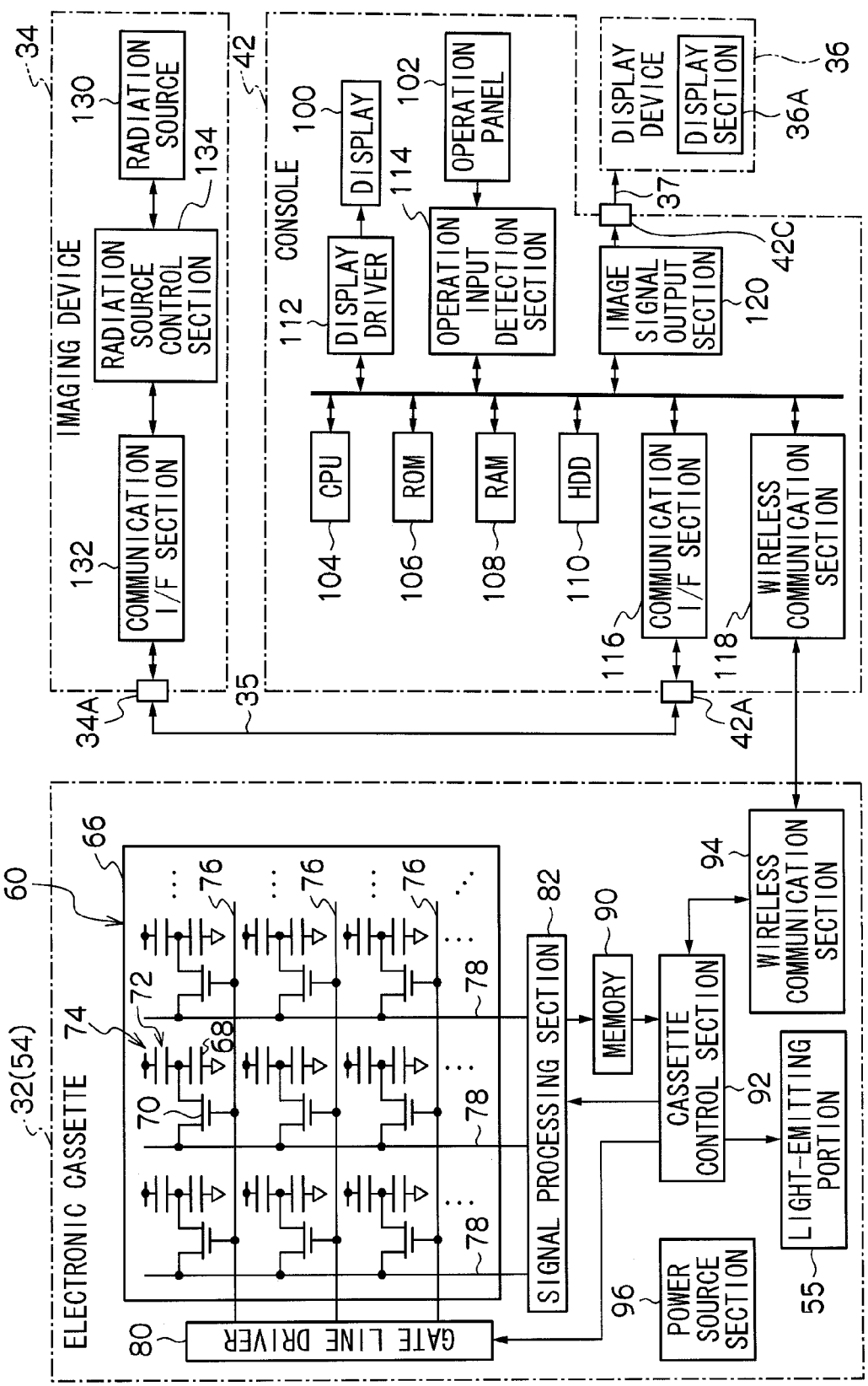
FIG. 5 is a block diagram showing the detailed structure of a radiographic imaging system relating to a first exemplary embodiment.

A block diagram showing the detailed structure of the radiographic imaging system 18 relating to the present exemplary embodiment is shown in FIG. 5.

A connection terminal 34A for carrying out communication with the console 42 is provided at the imaging device 34. A connection terminal 42A for carrying out communication with the imaging device 34, and a connection terminal 42C for outputting image signals to the display device 36, are provided at the console 42.

The imaging device 34 is connected to the console 42 via a communication cable 35, and the display device 36 is connected to the console 42 via a display cable 37.

The radiation detector 60 that is incorporated in the electronic cassette 32 is structured by layering a photoelectric converting layer, that absorbs the radiation X and converts it into charges, on a TFT active matrix substrate 66. The photoelectric converting layer is formed from, for example, an amorphous a-Se (amorphous selenium) whose main component is selenium (e.g., a content of greater than or equal to 50%). When the radiation X is irradiated, the photoelectric converting layer generates, at the interior thereof, charges (electron-hole pairs) of a charge amount corresponding to the irradiated radiation amount, and thereby converts the irradiated radiation X into charges. Note that, instead of a radiation-charge converting material that directly converts the radiation X into charges such as amorphous selenium, the radiation detector 60 may convert the radiation X into charges indirectly by using a fluorescent material and photoelectric converting elements (photodiodes). Gadolinium oxysulfide (GOS) and cesium iodide (CsI) are well known as fluorescent materials. In this case, conversion from the radiation X into light is carried out by the fluorescent material, and the conversion from light into charges is carried out by the photodiodes that are photoelectric converting elements.

Numerous pixel portions 74 having storage capacitors 68 that accumulate the charges generated at the photoelectric converting layer, and TFTs 70 for reading-out the charges accumulated in the storage capacitors 68, are arranged in the form of a matrix on the TFT active matrix substrate 66. In FIG. 5, the photoelectric converting layer corresponding to the individual pixel portions 74 is shown schematically as photoelectric converting portions 72. The charges, that are generated at the photoelectric converting layer accompanying the irradiation of the radiation X onto the electronic cassette 32, are accumulated in the storage capacitors 68 of the individual pixel portions 74. Due thereto, the image information, that is carried by the radiation X irradiated on the electronic cassette 32, is converted into charge information and is held at the radiation detector 60.

Plural gate lines 76, that extend in a given direction (the row direction) and are for turning the TFTs 70 of the individual pixel portions 74 on and off, and plural data lines 78, that extend in a direction (the column direction) orthogonal to the gate lines 76 and are for reading-out the accumulated charges from the storage capacitors 68 via the TFTs 70 that have been turned on, are provided at the TFT active matrix substrate 66. The individual gate lines 76 are connected to a gate line driver 80. The individual data lines 78 are connected to a signal processing section 82. When charges are accumulated in the storage capacitors 68 of the individual pixel portions 74, the TFTs 70 of the individual pixel portions 74 are turned on in order in units of rows by signals supplied from the gate line driver 80 via the gate lines 76. Then, the charges, that are accumulated in the storage capacitors 68 of the pixel portions 74 whose TFTs 70 have been turned on, are transferred through the data lines 78 as charge signals and are inputted to the signal processing section 82. Accordingly, the charges, that are accumulated in the storage capacitors 68 of the individual pixel portions 74, are read-out in order in units of rows.

Figure 6:
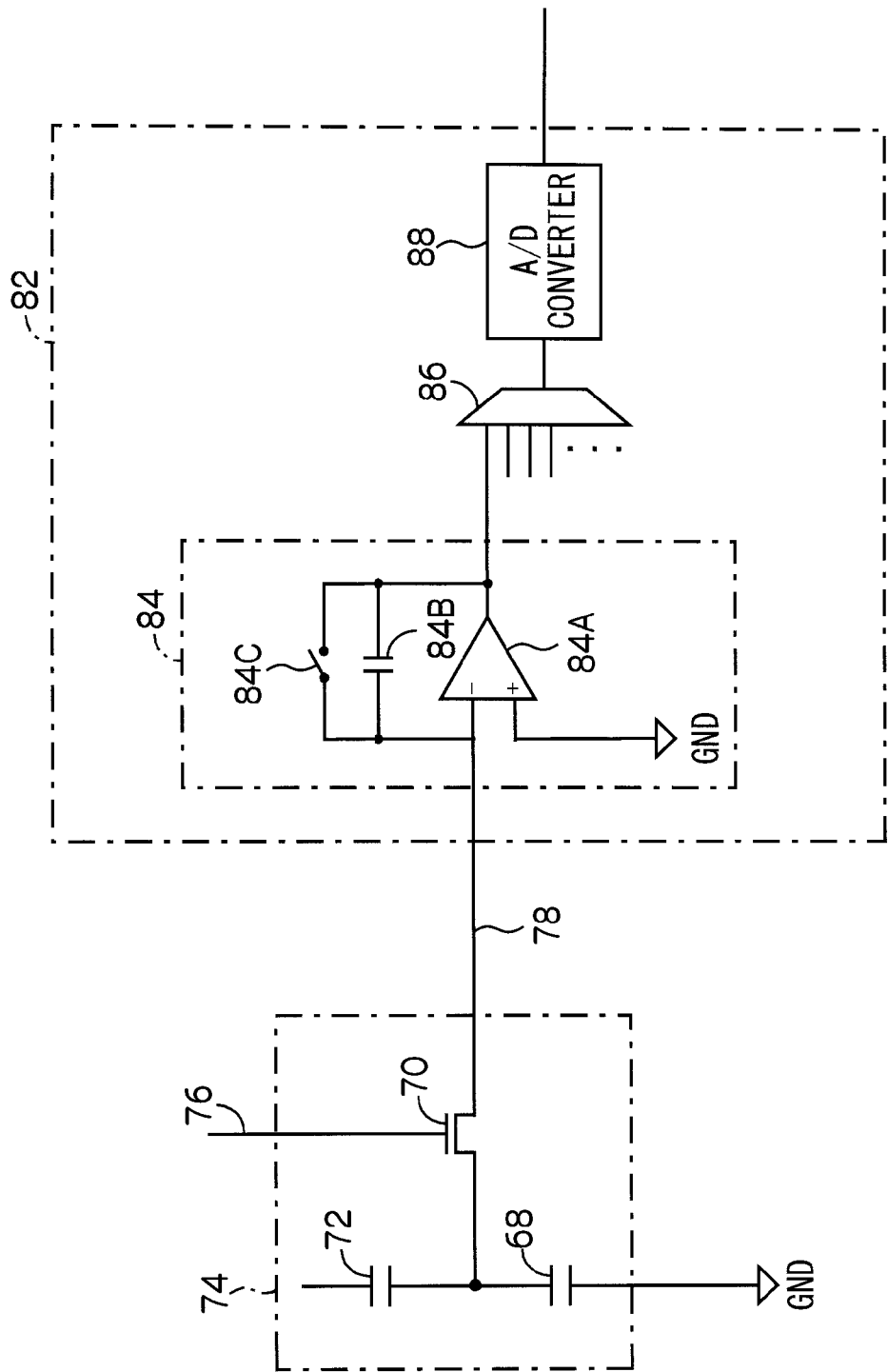
FIG. 6 is an equivalent circuit diagram that focuses on one pixel portion of a radiation detector relating to the exemplary embodiments.

An equivalent circuit diagram that focuses on one pixel portion of the radiation detector 60 relating to the present exemplary embodiment is shown in FIG. 6.

As shown in FIG. 6, the source of the TFT 70 is connected to the data line 78, and the data line 78 is connected to the signal processing section 82. Further, the drain of the TFT 70 is connected to the storage capacitor 68 and the photoelectric converting portion 72, and the gate of the TFT 70 is connected to the gate line 76.

The signal processing section 82 has a sample-and-hold circuit 84 for each of the individual data lines 78. The charge signals transferred through the individual data lines 78 are held by the sample-and-hold circuits 84. The sample-and-hold circuit 84 is structured to include an operational amplifier 84A and a capacitor 84B, and converts charge signals into analog voltage. Further, a switch 84C, that serves as a resetting circuit that shorts both electrodes of the capacitor 84B and discharges the charges accumulated at the capacitor 84B, is provided at the sample-and-hold circuit 84.

A multiplexer 86 and an A/D converter 88 are connected in that order to the output sides of the sample-and-hold circuits 84. The charge signals held in the individual sample-and-hold circuits are converted into analog voltages, are inputted in order (serially) to the multiplexer 86, and are converted into digital image information by the A/D converter 88.

A memory 90 is connected to the signal processing section 82 (see FIG. 5). The image information outputted from the A/D converter 88 of the signal processing section 82 is stored in order in the memory 90. The memory 90 has a storage capacity that can store image information, that express radiographic images, of an amount corresponding to a predetermined number of images. Each time reading-out of the charges of one line is carried out line-by-line, the image information of the read-out one line is successively stored in the memory 90.

The memory 90 is connected to a cassette control section 92 that controls the overall operation of the electronic cassette 32. The cassette control section 92 is realized by a microcomputer. A wireless communication section 94 is connected to the cassette control section 92. The wireless communication section 94 corresponds to wireless LAN (Local Area Network) standards such as IEEE (Institute of Electrical and Electronics Engineers) 802.11a/b/g or the like, and controls the transfer of various types of information with external devices by wireless communication. The cassette control section 92 can communicate wirelessly with the console 42 via the wireless communication section 94, such that the transmission and reception of various types of information to and from the console 42 is possible. The cassette control section 92 stores imaging control information, that will be described later and that is received from the console 42, and starts reading-out of charges on the basis of this information.

The light-emitting portion 55 is connected to the cassette control section 92. The light-emitting portion 55 incorporates therein a light-emitting element such as a light-emitting diode or the like, and emits light in accordance with control by the cassette control section 92.

Further, a power source section 96 is provided at the electronic cassette 32. The above-described various types of circuits and respective elements (the light-emitting portion 55, the gate line driver 80, the signal processing section 82, the memory 90, the wireless communication section 94, and the microcomputer that functions as the cassette control section 92) are operated by electric power supplied from the power source section 96. The power source section 96 incorporates therein a battery (a chargeable secondary battery) and supplies electric power to the various types of circuits and elements from the charged battery, so that the portability of the electronic cassette 32 is not adversely affected.

On the other hand, the console 42 is structured as a server computer. The console 42 has a display 100, that displays operation menus, captured radiographic images and the like, and an operation panel 102 that is structured to include plural keys and by which various types of information and operating instructions are inputted.

Further, the console 42 relating to the present exemplary embodiment includes: a CPU 104 that governs the operations of the overall device; a ROM 106 in which various types of programs, including control programs, and the like are stored in advance; a RAM 108 that temporarily stores various types of data; an HDD 110 that stores and holds various types of data; a display driver 112 that controls the display of various types of information on the display 100; an operation input detection section 114 that detects the operated state of the operation panel 102; a communication interface (I/F) section 116 that is connected to the connection terminal 42A and carries out transmission and reception of various types of information, such as exposure conditions and state information of the imaging device 34 and the like that will be described later, with the imaging device 34 via the connection terminal 42A and the communication cable 35; a wireless communication section 118 that carries out transmission and reception of various types of information, such as imaging control information and image information and the like, with the electronic cassette 32 by wireless communication; and an image signal output section 120 that is connected to the connection terminal 42C and outputs image signals to the display device 36 via the connection terminal 42C and the display cable 37.

The CPU 104, the ROM 106, the RAM 108, the HDD 110, the display driver 112, the operation input detection section 114, the communication I/F section 116, the wireless communication section 118 and the image signal output section 120 are connected to one another via a system bus BUS. Accordingly, the CPU 104 can access the ROM 106, the RAM 108 and the HDD 110, and can carry out control of display of various types of information on the display 100 via the display driver 112, control of transmission and reception of various types of information with the imaging device 34 via the communication I/F section 116, control of transmission and reception of various types of information with the electronic cassette 32 via the wireless communication section 118, and control of the image that is displayed at the display device 36 via the image signal output section 120. Further, the CPU 104 can grasp the operated state of the operation panel 102 by a user via the operation input detection section 114.

On the other hand, the imaging device 34 includes: a radiation source 130 that outputs the radiation X; a communication I/F section 132 that transmits and receives various types of information, such as exposure conditions and state information of the imaging device 34 and the like, with the console 42; and a radiation source control section 134 that controls the radiation source 130 on the basis of received exposure conditions. The radiation source control section 134 also is realized by a microcomputer, and stores the received exposure conditions, and causes the radiation X to be irradiated from the radiation source 130 on the basis of the stored exposure conditions.

The display device 36 includes a display section 36A that displays images expressed by received image signals.

Note that the first exemplary embodiment carries out visible display by using LCDs (Liquid Crystal Displays) as the display section 36A and the display 100, but is not limited to the same. Visible display may be carried out by using other displays such as organic EL displays, CRT displays or the like as the display section 36A and the display 100.

Next, the overall operation of the RIS 10 relating to the first exemplary embodiment will be briefly described.

The input terminal 12 (see FIG. 1) receives a imaging request, that includes environment information, from the surgeon 26 or radiology technician. The imaging request designates the environment in which the electronic cassette 32 is used, the imaging date and time, and the imaging conditions (the region that is image captured, the angle and number of shots, the tube voltage, tube current and irradiation time period for irradiating the radiation X, the size and sensitivity of the electronic cassette 32, and the like).

The input terminal 12 informs the RIS server 14 of the contents of the received imaging request. The RIS server 14 stores, in the database 28, the contents of the imaging request notified from the input terminal 12.

By accessing the RIS server 14, the console 42 acquires the contents of the imaging request and the environment information associated therewith from the RIS server 14, and displays the contents of the imaging request on the display 100 (see FIG. 2 and FIG. 5).

The surgeon 26 or the radiology technician starts capturing of radiographic images on the basis of the contents of the imaging request that are displayed on the display 100.

For example, as shown in FIG. 2, in a case of carrying out capturing of radiographic images of a portion to be treated of the patient 30 who is lying on the operating table 46, the surgeon 26 or the radiology technician places the electronic cassette 32 between the operating table 46 and the portion to be treated of the patient 30 in accordance with the region and angle of imaging, and places the imaging device 34 above the portion to be treated. Further, the surgeon 26 or the radiology technician carries out, at the operation panel 102 of the console 42, an exposure condition designating operation that designates the exposure conditions such as the tube voltage, the tube current, the irradiation time period and the like at the time of irradiating the radiation X, in accordance with the region to be imaged of the patient 30 and the imaging conditions. When exposure preparations of the imaging device 34 are completed, the surgeon 26 or the radiology technician carries out, at the operation panel 102 of the console 42, an imaging instructing operation that instructs imaging.

Next, the operation of the imaging system 18 relating to the first exemplary embodiment will be described in detail.

Figure 7:
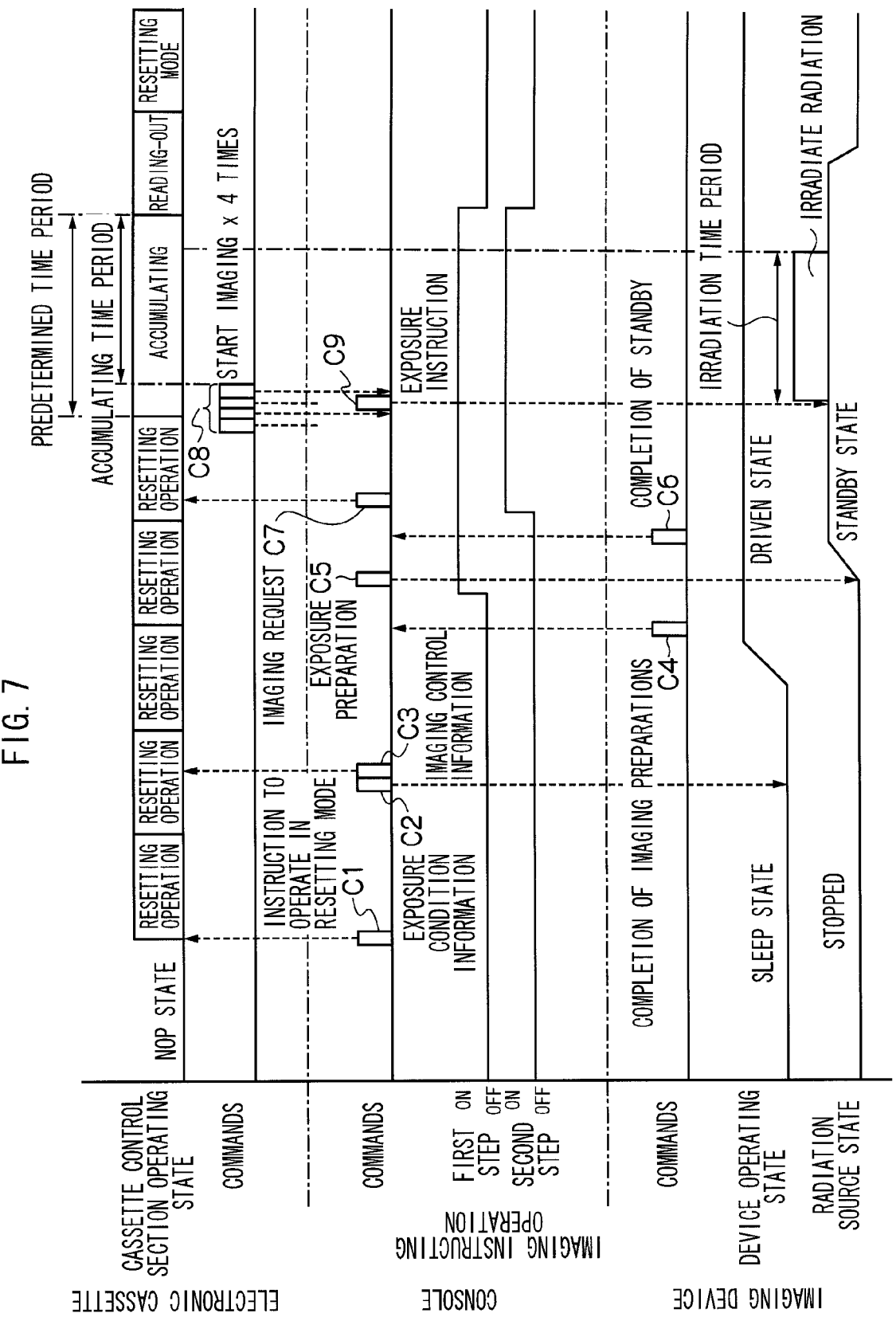
FIG. 7 is a timing chart showing the flow of operations at the time of capturing a radiographic image relating to the first exemplary embodiment.

A timing chart showing the flow of operations at the time of capturing a radiographic image by the imaging system 18 relating to the first exemplary embodiment is shown in FIG. 7.

In the state in which the power source of the electronic cassette 32 is turned on (the start-up state), the operation mode of the electronic cassette 32 is in a non-operating state (NOP state) that is an initial state, and the electronic cassette 32 operates on the basis of instruction information that is received from the console 42 by wireless communication.

When the power source of the electronic cassette 32 is in an on state, even if the radiation X is not being irradiated, at the radiation detector 60 (see FIG. 5) that is incorporated in the electronic cassette 32, charges are accumulated in the respective storage capacitors 68 due to dark current or the like. Therefore, when the operation mode is in the non-operating state, the cassette control section 92 is outputting an instruction signal that instructs resetting to the signal processing section 82. When the instruction signal that instructs resetting is inputted to the signal processing section 82, the switches 84C (see FIG. 6) turn on, and the both electrodes of the capacitors 84B are shorted. Due to the both electrodes of the capacitors 84B being shorted in this way, the charges that are accumulated unnecessarily in the capacitors 84B are discharged.

When the console 42 becomes able to communicate with the electronic cassette 32, the console 42 transmits instruction information C1, that instructs operation in the resetting mode, to the electronic cassette 32 by wireless communication.

At the cassette control section 92, when the instruction information C1 that instructs operation in the resetting mode is received, the operation mode moves on to the resetting mode, the gate line driver 80 is controlled such that on signals are outputted from the gate line driver 80 to the respective gate lines 76 in order and line-by-line, and the respective TFTs 36 that are connected to the respective gate lines 76 are turned on in order and line-by-line. Due thereto, the charges that are accumulated in the respective storage capacitors 68 flow-out to the respective data lines 78 as charge signals in order and line-by-line. During the time period when the operation mode is the resetting mode, the cassette control section 92 repeats the resetting operation in which on signals are made to be outputted to the respective gate lines 76 in order and line-by-line, and the charges of one frame that are accumulated in the respective storage capacitors 68 are reset.

When an exposure condition designating operation is carried out with respect to the operation panel 102, the console 42 transmits exposure condition information C2, such as the tube voltage, the tube current, the irradiation time period and the like that are designated by the exposure condition designating operation, to the imaging device 34 via the communication cable 35. Further, at the time of capturing of a radiographic image, the console 42 transmits imaging control information C3, such as the accumulating time period for accumulating charges in the respective storage capacitors 68 of the radiation detector 60 and the like, to the electronic cassette 32 by wireless communication.

At the imaging device 34, when the power source is turned on and a predetermined initial start-up operation is completed, the operating state of the imaging device 34 becomes a sleep state, and the imaging device 34 stands-by. When the exposure condition information C2 is received, the imaging device 34 stores the received exposure condition information, and the operating state moves on to a driven state. When the operating state returns to the driven state, the imaging device 34 transmits information C4, that expresses completion of imaging preparations, to the console 42 via the communication cable 35.

When the imaging control information C3 is received, the cassette control section 92 of the electronic cassette 32 stores the received imaging control information.

When the information C4 expressing completion of the imaging preparations is received, the console 42 displays the fact that imaging preparations have been completed on the display 100, and an imaging instructing operation that instructs imaging can be carried out with respect to the operation panel 102. In the imaging system 18 relating to the present exemplary embodiment, the imaging instructing operation with respect to the operation panel 102 is a two-step operation. Capturing of a radiographic image is carried out by carrying out the imaging instructing operation of the second step after the imaging instructing operation of the first step with respect to the operation panel 102. In this two-step imaging instructing operation, for example, two buttons of the operation panel 102 may be depressed in order, or, for example, a single button may be depressed halfway and then fully depressed.

When the imaging instructing operation of the first step is carried out on the operation panel 102, the console 42 transmits instruction information C5, that instructs preparation for exposure, to the imaging device 34 via the communication cable 35.

When the instruction information C5 that instructs preparation for exposure is received, the imaging device 34 carries out standby of the radiation source 130 so that exposure will be carried out at the tube voltage and the tube current shown by the exposure condition information that was stored immediately before. When standby of the radiation source 130 is completed, the imaging device 34 transmits information C6 that expresses completion of standby to the console 42 via the communication cable 35.

When the console 42 receives the information C6 expressing completion of standby, the imaging instructing operation of the second step becomes possible. When the imaging instructing operation of the second step is carried out on the operation panel 102, the console 42 transmits instruction information C7 that requests imaging to the electronic cassette 32 by wireless communication.

When the instruction information C7 requesting imaging is received, the cassette control section 92 causes the light-emitting portion 55 to emit light. Further, when the instruction information C7 requesting imaging is received, the cassette control section 92 carries out the resetting operation until the resetting operation of one frame is completed. After the resetting operation of one frame is completed, the cassette control section 92 transmits instruction information C8 that instructs starting of imaging to the console 42 by wireless communication, and moves the operation mode on to the imaging mode. Due to the light-emitting portion 55 being made to emit light in this way, the technician can be notified that the instruction information C7 requesting imaging has been received at the electronic cassette 32.

When the communication between the electronic cassette 32 and the console 42 is wireless communication as in the present exemplary embodiment, there are cases in which the state of the communication becomes unstable and the console 42 receives instruction information late or cannot receive instruction information.

Thus, the electronic cassette 32 relating to the present exemplary embodiment transmits the instruction information C8, that instructs starting of imaging and that includes identification information for identifying which (i.e., first, second, etc.) transmission number it is, plural times by wireless communication at a predetermined cycle, even during a response wait time period in which a response such as ACK (ACKnowledgement) or the like is returned. This predetermined cycle may be each uniform interval, or may be made to be longer each time that the instruction information is transmitted one time (e.g., may be made to be twice the interval of the previous time, or the like).

By transmitting plural times the instruction information C8 that instructs starting of imaging from the electronic cassette 32 in this way, even if the communication state is unstable, exposure can be started if any of the instruction information C8 is received at the console 42. Therefore, capturing of radiographic images can be carried out stably.

FIG. 7 illustrates a case in which, among the instruction information C8 that are transmitted four times from the electronic cassette 32, the instruction information of the second time and the fourth time are received at the console 42.

When any of the instruction information C8, that instruct starting of imaging and are transmitted plural times, is received, the console 42 transmits instruction information C9 that instructs exposure to the imaging device 34 via the communication cable 35.

When the instruction information C9 instructing exposure is received, the imaging device 34 irradiates the radiation X from the radiation source 130 for the irradiation time period expressed by the exposure condition information that was stored immediately before.

Figure 8:
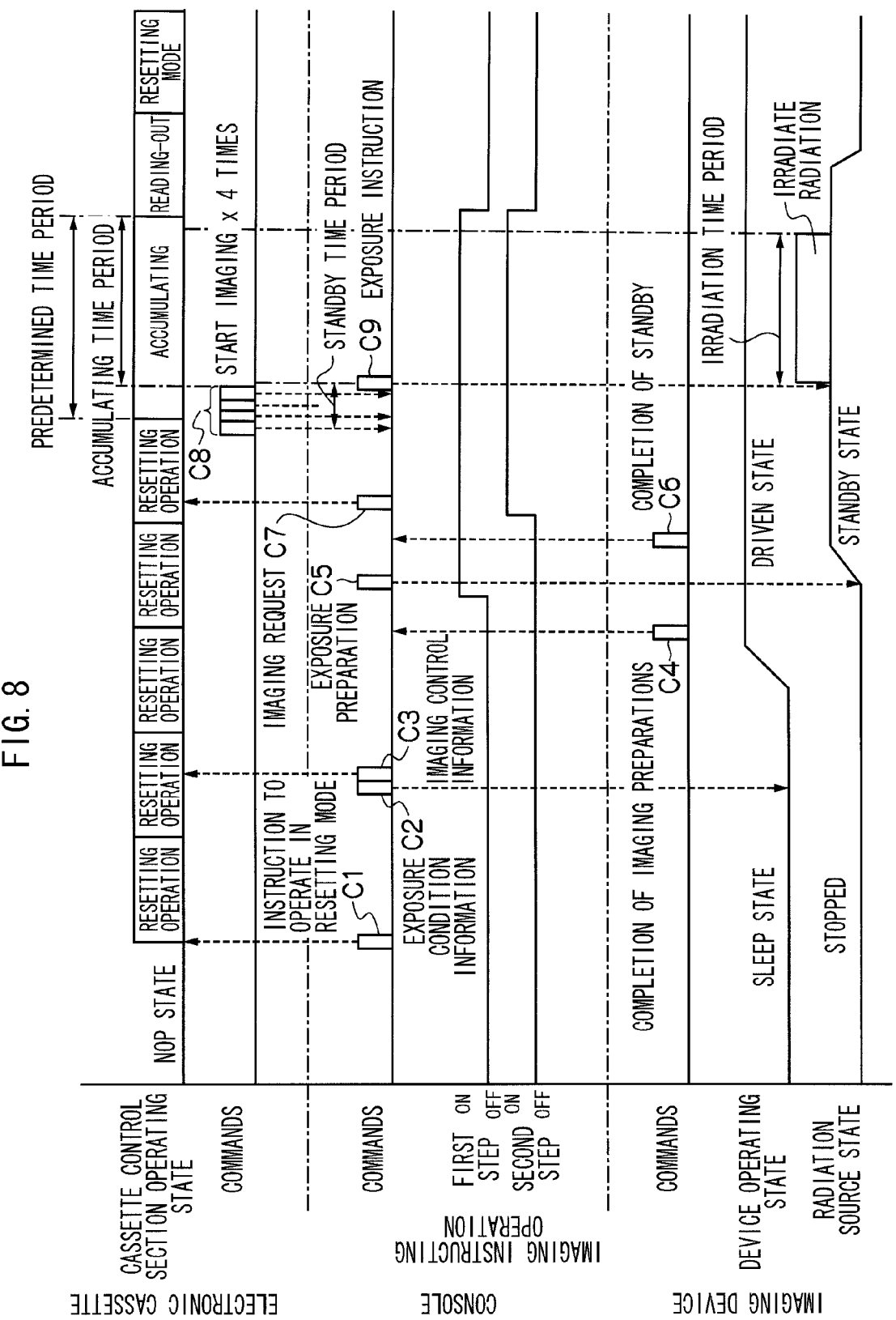
FIG. 8 is a timing chart showing the flow of operations at the time of capturing a radiographic image relating to another exemplary embodiment.

Note that the console 42 may change the time of transmitting the instruction information C9 instructing exposure, so that the time at which the radiation X is irradiated from the radiation source 130 becomes constant. For example, as shown in FIG. 8, the console 42 transmits the instruction information C9 instructing exposure after a predetermined standby time period from the receipt of the instruction information C8 of the first time instructing the start of imaging. In this case, if the instruction information C8 of the first time instructing the start of imaging is not received at the console 42 and the instruction information C8 of the second time instructing the start of imaging is received, the standby time period is shortened by an amount corresponding to the cycle at which the instruction information C8 of the first time and the second time are transmitted. Due thereto, the time at which the radiation X is irradiated from the radiation source 130 can be made to be constant.

The radiation X irradiated from the radiation source 130 is transmitted through the patient 30, and thereafter, reaches the electronic cassette 32. Due thereto, charges, that correspond to the radiation amount of the irradiated radiation X, are accumulated in the storage capacitors 68 of the respective pixel portions 74 of the radiation detector 60 incorporated in the electronic cassette 32.

After transmitting the instruction information C8 that instructs starting of imaging, the cassette control section 92 stands-by for a predetermined time period, and thereafter, controls the gate line driver 80 such that on signals are outputted from the gate line driver 80 to the respective gate lines 76 in order and line-by-line, and the respective TFTs 36 connected to the respective gate lines 76 are turned on in order and line-by-line. This predetermined time period is a time period from after the transmission of the last instruction information C8, among the instruction information C8 that instruct starting of imaging and that are transmitted plural times, until the accumulating time period, that is prescribed by the imaging control information that was stored immediately before, has elapsed. Due thereto, even in cases in which only the final instruction information C8 is received at the console 42 and the radiation X is irradiated from the radiation source 130, the radiation X can be irradiated at least for the accumulating time period that is necessary for imaging and is prescribed by the imaging control information.

Note that, in a case in which adjustment is carried out such that the time at which the radiation X is irradiated from the radiation source 130 becomes constant as described above, reading-out of the image information may be started after standing-by for the aforementioned accumulating time period from the time that the radiation X is irradiated. This time at which the radiation X is irradiated is, for example, the time after the aforementioned standby time period from the transmission of the instruction information C8 of the first time instructing starting of imaging at the electronic cassette 32.

Figure 9:
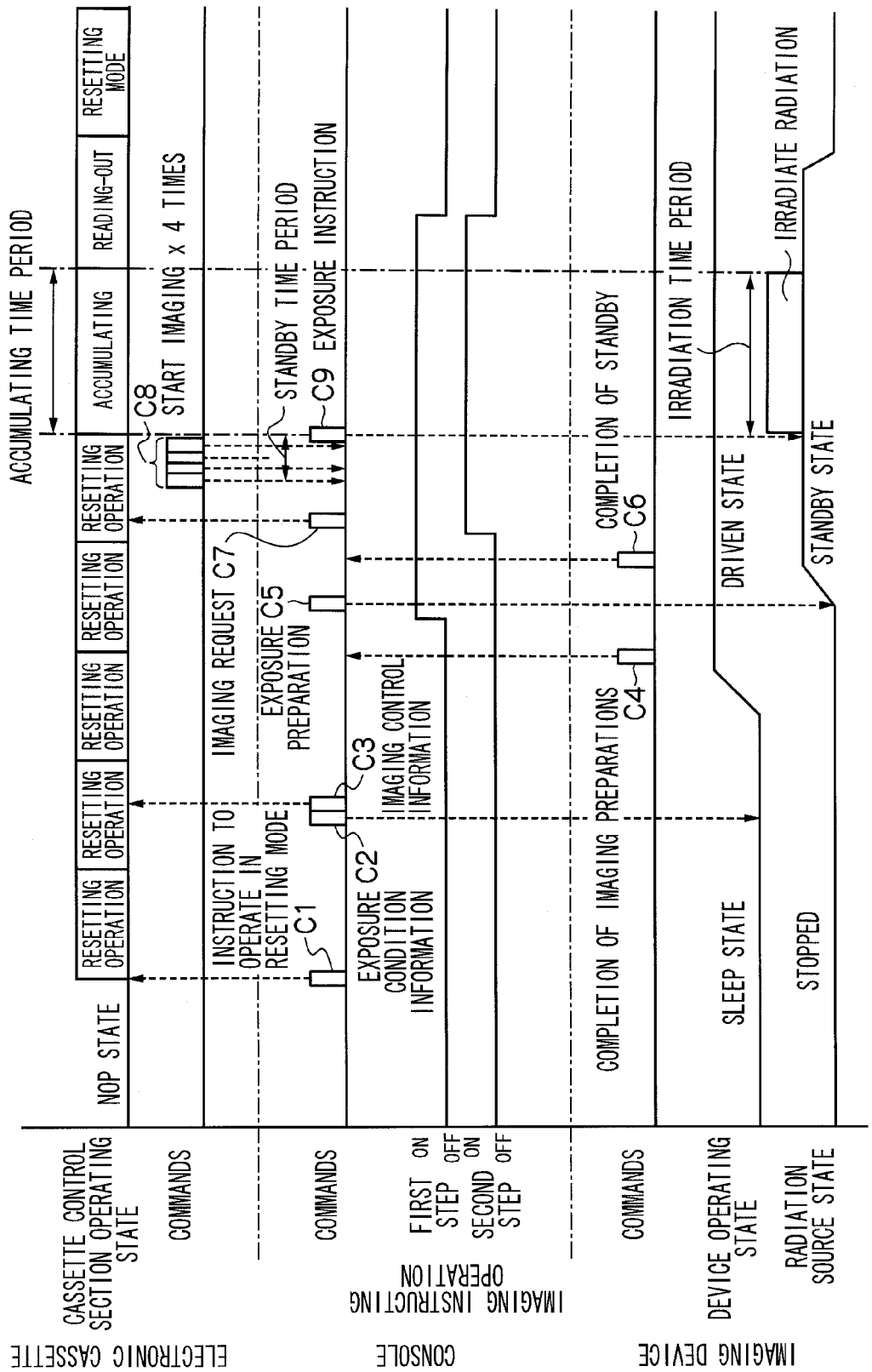
FIG. 9 is a timing chart showing the flow of operations at the time of capturing a radiographic image relating to yet another exemplary embodiment.

Further, in a case in which adjustment is carried out such that the time at which the radiation X is irradiated from the radiation source 130 becomes constant, the time of starting the transmission of the instruction information C8 instructing starting of imaging from the electronic cassette 32 may be made to be earlier as shown in FIG. 9. The operation of the electronic cassette 32 of resetting one frame is repeated at a fixed cycle. Therefore, the time of starting the transmission of the instruction information C8 instructing starting of imaging from the electronic cassette 32 may be made to be earlier, within the range of the aforementioned standby time period, than the time at which the resetting operation of one frame is completed. By making the time of starting the transmission of the instruction information C8 earlier in this way, the time of the start of the accumulating time period of the charges and the time at which the radiation x is irradiated from the radiation source 130 can be made to be closer to one another. The need to wait superfluously for the accumulation of charges is eliminated, and therefore, the amount of noise can be reduced.

At the radiation detector 60, when the respective TFTs 36 connected to the respective gate lines 76 are turned on in order and line-by-line, the charges that are accumulated in the respective storage capacitors 68 flow-out to the respective data lines 78 as charge signals in order and line-by-line. The charge signals, that flow-out to the respective data lines 78, are inputted to the individual sample-and-hold circuits 84 and converted into voltage signals, and the converted voltage signals are inputted in order (serially) to the multiplexer, are converted into digital image information by the A/D converter, and are stored in the memory 90.

At the cassette control section 92, when the reading-out of the image information of one frame (one shot) has ended, the operating mode moves on to the resetting mode. Here, it is assumed that continuous imaging is not carried out and that the operation mode moves on to the resetting mode. However, continuous imaging may be carried out.

When the irradiation of the radiation X from the radiation source 130 ends, the console 42 transmits an image information transfer request signal to the electronic cassette 32 by wireless communication.

When the image information transfer request signal is received, the cassette control section 92 transmits, to the console 42 and frame-by-frame, the image information of one frame that is stored in the memory 90.

The console 42 carries out predetermined image processing on the image information of one frame, and stores the image information after the image processing in the HDD 110 in a state of being associated with the patient information of the patient 30. Further, the console 42 outputs, to the display device 36, image signals that express the radiographic image after the image processing, and causes the radiographic image to be displayed on the display section 36A of the display device 36. The surgeon 26 performs the surgery while confirming the radiographic image displayed on the display section 36A.

As described above, in accordance with the first exemplary embodiment, at the time when preparations for capturing a radiographic image are completed, the electronic cassette 32 transmits, plural times and by wireless communication, the instruction information C8 that instructs the starting of imaging. When the console 42 receives any of the instruction information C8 that have been transmitted plural times, the console 42 controls the imaging device 34 so that radiation is irradiated with respect to the electronic cassette 32. Therefore, capturing of radiographic images can be carried out stably even in cases in which the communication between the electronic cassette 32 and the console 42 is wireless communication.

Further, in accordance with the first exemplary embodiment, when the electronic cassette 32 receives the instruction information C7 requesting imaging, the electronic cassette 32 causes the light-emitting portion 55 to emit light. The technician can thereby discern that the instruction information C7 has been received at the electronic cassette 32. In particular, if the instruction information C7 cannot be received at the electronic cassette 32, the imaging instructing operation must be repeated which causes a great burden. Therefore, it is preferable that the technician be able to discern that the instruction information C7 has been received at the electronic cassette 32.

Moreover, in accordance with the first exemplary embodiment, it is easy for the handle 54A to be exposed even if the electronic cassette 32 is placed between the operating table 46 and the portion to be treated of the patient 30. Therefore, by providing the light-emitting portion 55 at the handle 54A of the electronic cassette 32, it is easy to see the light-emitting portion 55.

Second Exemplary Embodiment

A second exemplary embodiment of the present invention will be described next.

Because the structure of the radiation information system 10 and the structure of the electronic cassette 32 relating to the second exemplary embodiment are the same as those of the above-described first exemplary embodiment (see FIG. 1 through FIG. 6), description thereof will be omitted here.

Figure 10:
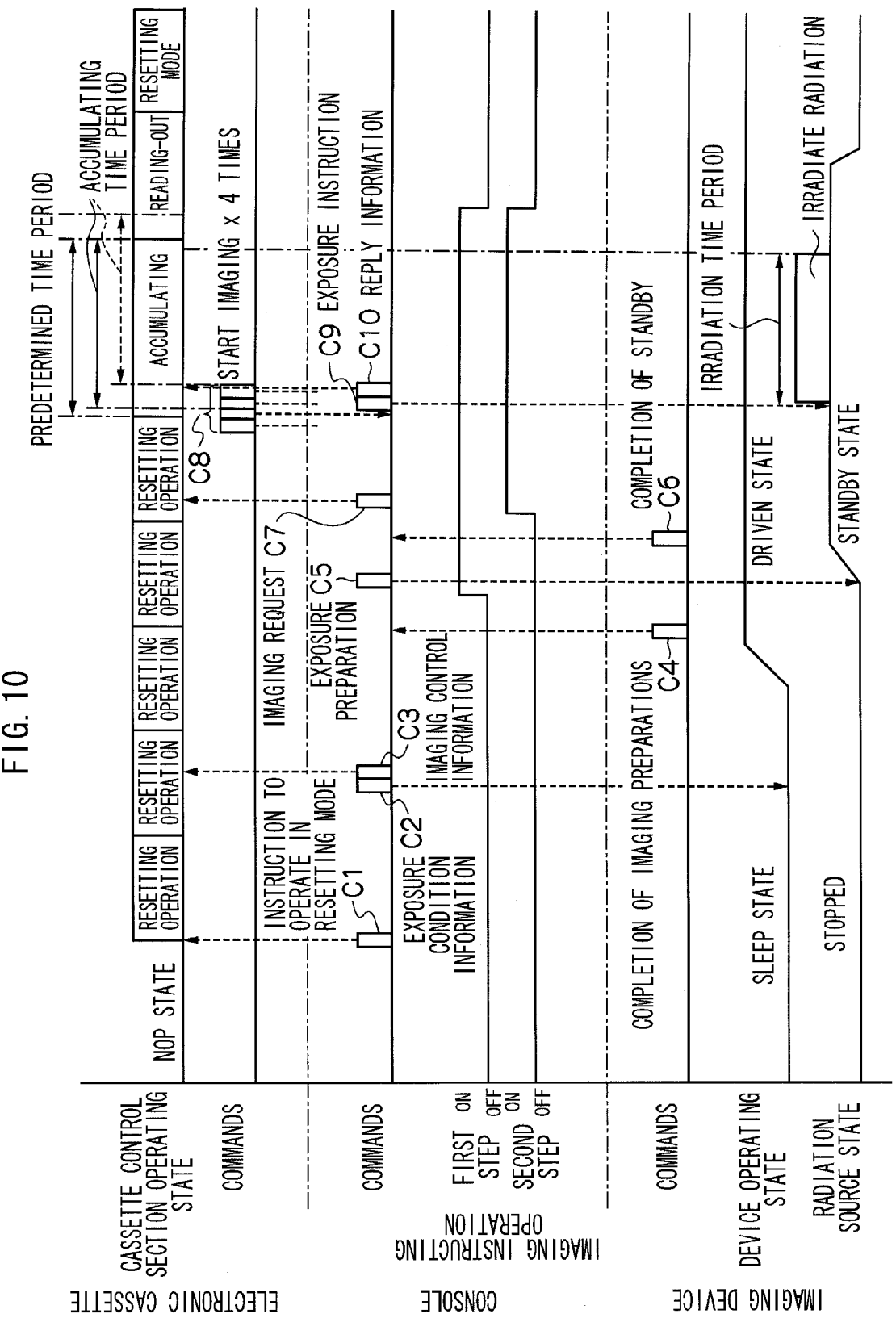
FIG. 10 is a timing chart showing the flow of operations at the time of capturing a radiographic image relating to a second exemplary embodiment.

A timing chart showing the flow of operations at the time of capturing a radiographic image by the imaging system 18 relating to the second exemplary embodiment is shown in FIG. 10. Note that portions that are the same as those of the above-described first exemplary embodiment (FIG. 7) are denoted by the same reference numerals, and description thereof is omitted.

The electronic cassette 32 relating to the present exemplary embodiment as well transmits the instruction information C8, that instructs starting of imaging and includes identification information for identifying which time number (i.e., first, second, etc.) the transmission is, plural times by wireless communication at a predetermined cycle even during a response wait time period.

When the console 42 receives any of the instruction information C8 that instruct starting of imaging and are transmitted plural times, the console 42 transmits the instruction information C9 instructing exposure to the imaging device 34 via the communication cable 35, and transmits reply information C10, that includes the identification information included in the instruction information that was received initially, to the electronic cassette 32 by wireless communication. Note that the identification information itself may be transmitted as the reply information C10. It suffices for the reply information C10 to include information expressing which (i.e., the first, second, etc.) of the transmitted instruction information C8 was received.

When the instruction information C9 instructing exposure is received, the imaging device 34 causes the radiation X to be irradiated from the radiation source 130 for the irradiation time period expressed by the exposure condition information that was stored immediately before.

The radiation X that is irradiated from the radiation source 130 is transmitted through the patient 30, and thereafter, reaches the electronic cassette 32. Due thereto, charges, that correspond to the radiation amount of the irradiated radiation X, are accumulated in the storage capacitors 68 of the respective pixel portions 74 of the radiation detector 60 incorporated in the electronic cassette 32.

After transmitting the instruction information C8 that instructs starting of imaging, the cassette control section 92 stands-by for the aforementioned predetermined time period, and thereafter, controls the gate line driver 80 such that on signals are outputted from the gate line driver 80 to the respective gate lines 76 in order and line-by-line, and the respective TFTs 36 connected to the respective gate lines 76 are turned on in order and line-by-line.

In a case in which the cassette control section 92 receives reply information from the console 42 during this predetermined time period, the cassette control section 92 changes the predetermined time period to a time period that is from after transmission of the instruction information C8, that instructs starting of imaging and includes the identification information included in that reply information, until the accumulating time period, that is prescribed by the imaging control information stored immediately before, elapses. In FIG. 10, because the instruction information C8 of the second time is received at the console 42, the predetermined time period is changed to a time period that is from the instruction information C8 of the second time until the accumulating time period elapses.

As described above, in accordance with the second exemplary embodiment, identification information that is included in the reply information shows the time number (i.e., first, second, etc.) of the instruction information that was received at the console 42 among the instruction information that instruct starting of imaging and were transmitted plural times. When the console 42 receives the instruction information instructing starting of imaging, the console 42 transmits instruction information instructing exposure to the imaging device 34 and causes the imaging device 34 to carry out exposure. Therefore, if charges are accumulated during the accumulating time period that is prescribed by the imaging control information from the receipt of the instruction information at the console 42, a radiographic image can be obtained. The need to superfluously wait for the accumulation of charges is eliminated, and therefore, the amount of noise can be reduced.

Third Exemplary Embodiment

A third exemplary embodiment of the present invention will be described next.

Because the structure of the radiation information system 10 and the structure of the electronic cassette 32 relating to the third exemplary embodiment are the same as those of the above-described first exemplary embodiment (see FIG. 1 through FIG. 6), description thereof will be omitted here.

Figure 11:
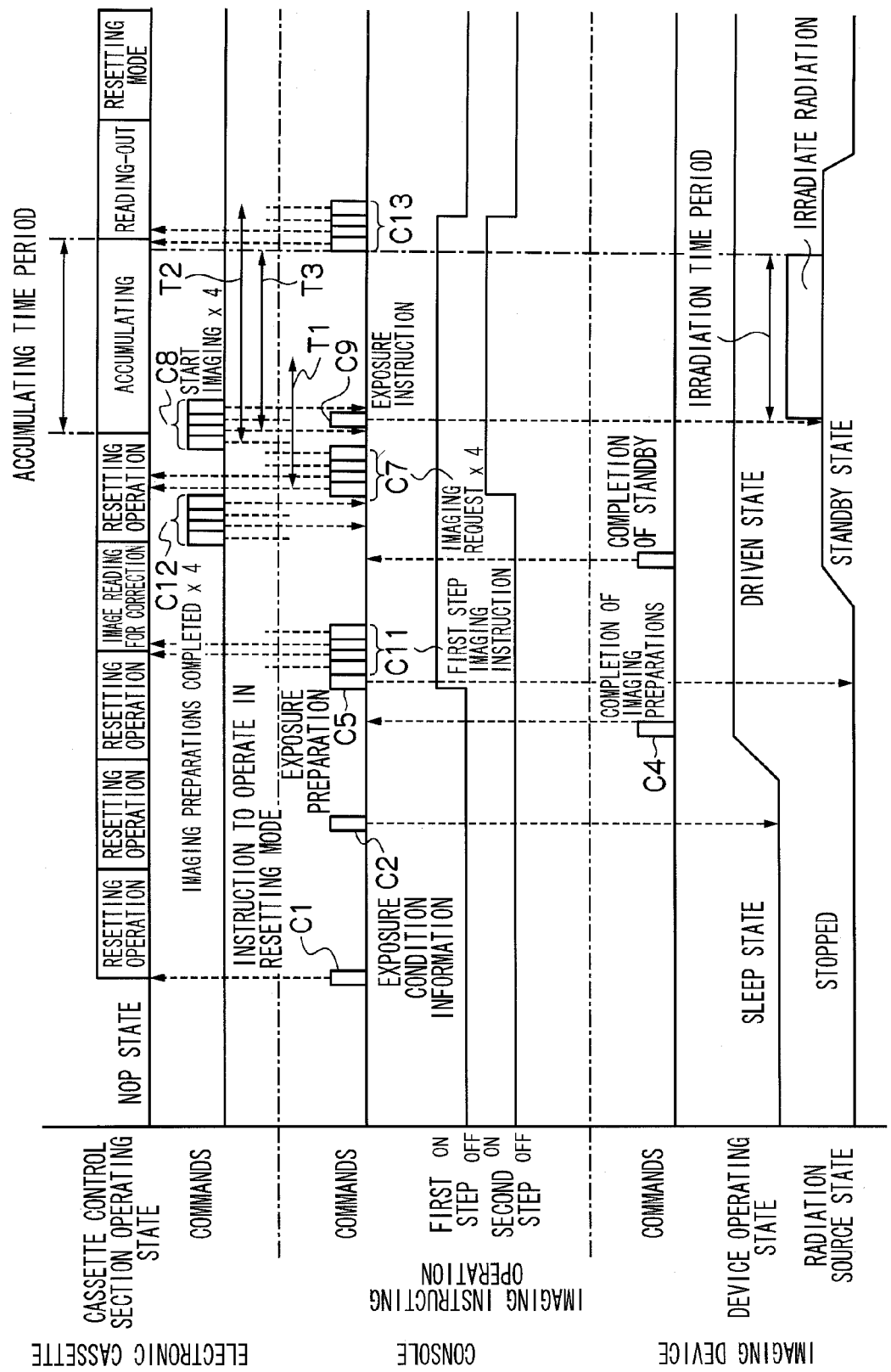
FIG. 11 is a timing chart showing the flow of operations at the time of capturing a radiographic image relating to a third exemplary embodiment.

A timing chart showing the flow of operations at the time of capturing a radiographic image by the imaging system 18 relating to the third exemplary embodiment is shown in FIG. 11. Note that portions that are the same as those of the above-described first exemplary embodiment (FIG. 7) are denoted by the same reference numerals, and description thereof is omitted.

In the present exemplary embodiment, when an exposure condition designating operation is carried out with respect to the operation panel 102, the console 42 transmits the exposure condition information C2, such as the tube voltage, the tube current, the irradiation time period and the like that are designated by the exposure condition designating operation, to the imaging device 34 via the communication cable 35, and does not carry out transmission of the imaging control information C3.

Here, at the radiation detector 60 (see FIG. 5) that is incorporated in the electronic cassette 32, there are cases in which charges that are generated at the photoelectric converting layer (the photoelectric converting portions 72) are trapped within the photoelectric converting layer and an after-image is generated.

Further, as mentioned in Japanese Patent No. 3264693 for example, there are cases in which the frequency of a reset clock signal is switched at a resetting time period and a data reading time period.

Thus, when the imaging instructing operation of the first step is carried out with respect to the operation panel 102, the console 42 relating to the present exemplary embodiment transmits the instruction information C5 instructing exposure preparation to the imaging device 34 via the communication cable 35, and transmits instruction information C11, that expresses that the imaging instructing operation of the first step has been carried out, plural times (four times in the present exemplary embodiment) to the electronic cassette 32 by wireless communication even during a response wait time period. By transmitting plural times the instruction information C11 that expresses that the imaging instructing operation of the first step has been carried out in this way, the instruction information C11 is easily relayed even in cases in which the communication state of the wireless communication becomes unstable. Therefore, the user (imaging operator) can smoothly carry out the imaging operation.

When any of the instruction information C11 that are transmitted plural times is received, the cassette control section 92 carries out the resetting operation until the resetting operation of one frame is completed. After completion of the resetting operation of one frame, in order to obtain image information expressing an after-image, the gate line driver 80 is controlled such that on signals are outputted from the gate line driver 80 to the respective gate lines 76 in order and line-by-line, and reading-out of the image information is carried out. The read-out image information is stored in the memory 90 as image information for after-image correction. Note that, in a case in which any of the instruction information C11 that are transmitted plural times is received, the cassette control section 92 may change the cycle or the time period of the resetting as described in Japanese Patent No. 3264693.

When the image information for after-image correction is stored in the memory 90, the cassette control section 92 transmits information C12, that expresses completion of preparations for imaging, plural times (four times in the present exemplary embodiment) to the console 42 by wireless communication even during a response wait time period. Note that the cassette control section 92 may transmit the information C12, that expresses completion of imaging preparations, at the time when any of the instruction information C11 is received.

When the console 42 receives the information C6 expressing standby completion from the imaging device 34 and receives any of the information C12, that express completion of imaging preparations and were transmitted plural times, from the electronic cassette 32, the imaging instructing operation of the second step becomes possible.

When the imaging instructing operation of the second step is carried out with respect to the operation panel 102, the console 42 transmits the instruction information C7, that requests imaging, plural times (four times in the present exemplary embodiment) to the electronic cassette 32 by wireless communication even during a response wait time period. By transmitting plural times the instruction information C7 requesting imaging in this way, the instruction information C7 is easily relayed even in cases in which the communication state of the wireless communication becomes unstable. Therefore, the imaging timing becoming offset can be suppressed.

When the instruction information C7 requesting imaging is received, the cassette control section 92 causes the light-emitting portion 55 to emit light, and carries out the resetting operation until the resetting operation of one frame is completed. After completion of the resetting operation of one frame, the cassette control section 92 transmits the instruction information C8, that instructs starting of imaging, plural times to the console 42 by wireless communication at a predetermined cycle, and the operation mode moves on to the imaging mode.

When any of the instruction information C8 instructing the starting of imaging is received, the console 42 transmits the instruction information C9 instructing exposure to the imaging device 34 via the communication cable 35 so as to cause exposure to be carried out.

When the instruction information C9 instructing exposure is received, the imaging device 34 irradiates the radiation X from the radiation source 130 for the irradiation time period expressed by the exposure condition information that was stored immediately before.

If there is a long time period from the time when the surgeon 26 or the radiology technician carries out the imaging instructing operation of the second step that instructs imaging with respect to the operation panel 102 to the time when the imaging device 34 actually carries out exposure, there are cases in which the patient 30 moves, and a radiographic image of the desired position cannot be obtained.

Thus, after transmitting the instruction information C7 requesting imaging, if the console 42 receives any of the instruction information C8 instructing starting of imaging within a predetermined imaging standby time period T1, the console 42 transmits the instruction information C9 and causes the imaging device 34 to carry out exposure. If the console 42 does not receive any of the instruction information C8 within the imaging standby time period T1, the console 42 does not transmit the instruction information C9, and displays on the display 100 the fact that time has run out. A time period that is determined in advance by experimentation using an actual device, or by computer simulation based on design specifications or the like, or the like, is used as the imaging standby time period T1.

In this way, by discontinuing exposure in a case in which none of the instruction information C8 are received within the imaging standby time period T1, imaging is discontinued in a case in which there is a large time lag between the imaging instructing time at which the imaging instructing operation of the second step is carried out and the exposure timing, and there is the concern that the patient 30 may move.

After the irradiation time period, that is expressed by the exposure condition information, has elapsed from the time that the console 42 transmits the instruction information C9 instructing exposure to the imaging device 34, the console 42 transmits instruction information C13, that instructs reading-out of charges, plural times (four times in the present exemplary embodiment) to the electronic cassette 32 by wireless transmission even during a response wait time period. Note that the imaging device 34 may inform the console 42 of the end of exposure, and the console 42 may, after receiving notice of the end of exposure from the imaging device 34, transmit the instruction information C13 instructing reading-out of charges. Or, the console 42 may, after standing-by for at least a predetermined irradiation standby time period T3 from receipt of the instruction information C9 instructing exposure, transmit the instruction information C13 that instructs reading-out of charges, so that the instruction information C13 instructing reading-out of charges is not erroneously transmitted during the irradiating of the radiation from the imaging device 34. This irradiation standby time period T3 may be the shortest irradiation time period among the irradiation time periods corresponding to the respective regions of imaging.

When any of the instruction information C13 instructing reading-out of charges is received, the cassette control section 92 controls the gate line driver 80 such that on signals are outputted from the gate line driver 80 to the respective gate lines 76 in order and line-by-line, and the respective TFTs 36 connected to the respective gate lines 76 are turned on in order and line-by-line.

At the radiation detector 60, when the respective TFTs 36 connected to the respective gate lines 76 are turned on in order and line-by-line, the charges that are accumulated in the respective storage capacitors 68 flow-out to the respective data lines 78 as charge signals in order and line-by-line. The charge signals, that flow-out to the respective data lines 78, are inputted to the individual sample-and-hold circuits 84 and converted into voltage signals, and the converted voltage signals are inputted in order (serially) to the multiplexer, are converted into digital image information by the A/D converter, and are stored in the memory 90.

At the cassette control section 92, when the reading-out of the image information of one frame (one shot) has ended, the cassette control section 92 carries out after-image correction processing by determining the difference in images between this image information and the image information for after-image correction that was previously stored in the memory 90, and stores the image information after the correction processing in the memory 90 as the captured image.

By the way, if the instruction information C13 instructing reading-out of charges is not transmitted from the console 42, the cassette control section 92 remains as is in a charge accumulated state.

Thus, the cassette control section 92 starts the reading-out of charges in a case in which the instruction information C13 instructing reading-out of charges is not received even while standing-by during a predetermined accumulating standby time period T2 after the start of the transmission of the instruction information C8 instructing the starting of imaging. A time period that is determined in advance by experimentation using an actual device, or by computer simulation based on design specifications or the like, or the like, is used as the accumulating standby time period T2.

By starting the reading-out of the charges in a case in which the instruction information C13 instructing reading-out of charges is not received even while standing-by during the accumulating standby time period T2 in this way, it is possible to prevent reading-out of a radiographic image from not being carried out although exposure has been carried out, and to prevent a delay in the reading-out of the radiographic image.

Further, in accordance with the third exemplary embodiment, by transmitting plural times various types of information that are wirelessly communicated between the electronic cassette 32 and the console 42, capturing of radiographic images can be carried out stably even in cases in which the communication state of the wireless communication has become unstable.

Note that the above-described respective exemplary embodiments describe cases of application to an electronic cassette that is a portable radiographic imaging device. However, the present invention is not limited to the same, and may be applied to a stationary radiographic imaging device.

Further, the above second exemplary embodiment describes a case in which, when the reply information is received, changes are carried out to shorten the predetermined time period to the time period that is from after transmission of the instruction information C8, that instructs the starting of imaging and includes the identification information included in the reply information, until the accumulating time period has elapsed. However, the present invention is not limited to the same. For example, in a case in which the predetermined time period is made to be the time period from after the transmission of the initial instruction information C8, among the instruction information C8 that instruct starting of imaging and that are transmitted plural times, until the accumulating time period has elapsed, when the reply information is received, changes may be carried out to lengthen the predetermined time period to a time period that is from after the transmission of the instruction information C8, that instructs starting of imaging and that includes the identification information included in that reply information, until the accumulating time period has elapsed.

Further, the above respective exemplary embodiments describe cases in which the light-emitting portion 55 is made to emit light in a case in which the instruction information C7 is received at the electronic cassette 32. However, the present invention is not limited to the same. For example, the light-emitting portion 55 may be made to emit light also in cases in which other information, such as the instruction information C1 instructing operation in the resetting mode, or the imaging control information C3, or the like is received. In this case, in order to identify which information has been received, the light-emitting pattern of the light-emitting portion 55 may be varied in accordance with the received information. Or, a speaker or the like may be provided, and notice may be given by sound.

Moreover, the above respective exemplary embodiments describe cases in which the second notification section, such as the light-emitting portion 55 or the like, is provided at the electronic cassette 32, and notice is given of the status of reception of information by wireless communication. However, notice may be given of the status of reception of information by wireless communication by providing the second notification section at the console 42.

In addition, the structure of the radiation information system 10 (see FIG. 1), the structure of the imaging system 18 (see FIG. 2 and FIG. 5), and the structure of the electronic cassette 32 (see FIG. 3 and FIG. 4) that are described in the above respective exemplary embodiments are examples, and can of course be changed in accordance with the situation and within a scope that does not deviate from the gist of the present invention.

Further, the flows (see FIG. 7 through FIG. 10) of the operations at the time of capturing a radiographic image, that are described in the above respective exemplary embodiments, are also examples, and can of course be changed in accordance with the situation and within a scope that does not deviate from the gist of the present invention.

What is claimed is:

1. A radiographic imaging system comprising:
a radiographic imaging device comprising a generating section that captures a radiographic image expressed by irradiated radiation and generates image information expressing the captured radiographic image, and a first communication section that transmits, plural times and by wireless communication and even during a response wait time period, imaging start instructing information that instructs starting of imaging at a time when preparations for capturing a radiographic image by the generating section have been completed; and
a control device having a second communication section that is able to communicate by wireless communication with the first communication section, and a control section that controls a radiation irradiating section such that radiation is irradiated with respect to the radiographic imaging device in a case in which the second communication section receives any of the imaging start instructing information that are transmitted plural times from the first communication section.

2. The radiographic imaging system of claim 1, wherein the first communication section transmits, at a predetermined cycle, the imaging start instructing information that includes identification information for identifying the number of times of transmissions.

3. The radiographic imaging system of claim 2, wherein the control section changes a time of causing radiation to be irradiated from the radiation irradiating section, on the basis of the identification information that is included in the imaging start instructing information received at the second communication section.

4. The radiographic imaging system of claim 2, wherein
the generating section has plural charge storing sections that accumulate charges generated by radiation being irradiated, and in which charges are respectively accumulated in accordance with an accumulating time period of the charges, and
the first communication section transmits the imaging start instructing information at a time of resetting the charges accumulated in the plural charge storing sections.

5. The radiographic imaging system of claim 4, wherein
the control section effects control such that, in a case in which the imaging start instructing information is received at the second communication section, reply information is transmitted from the second communication section to the first communication section on the basis of the identification information included in the received imaging start instructing information, and
in a case in which the first communication section receives the reply information, the generating section changes a time period for accumulating charges at the charge storing sections at a time of capturing a radiographic image, on the basis of the returned reply information.

6. The radiographic imaging system of claim 1, wherein
the control device further has a receiving section that receives, in two steps, radiographic imaging instructing operations by the generating section, and
in at least one case in which an imaging instructing operation of a first step and an imaging instructing operation of a second step are received at the receiving section, the control section transmits, plural times and by wireless communication and even during a response wait time period and from the second communication section, imaging instructing information that corresponds to the step of the imaging instructing operation.

7. The radiographic imaging system of claim 6, wherein the control device further has a first notification section that gives notice in a case in which the imaging start instructing information is not received even while standing-by during a predetermined imaging standby time period from transmission of the imaging instructing information that corresponds to the imaging instructing operation of the second step.

8. The radiographic imaging system of claim 4, wherein
in a case in which the imaging start instructing information is received at the second communication section, the control section controls the radiation irradiating section, and effects control such that read-out instructing information, that instructs starting of reading-out of accumulated charges, is transmitted from the second communication section to the first communication section after ending of irradiation of radiation from the radiation irradiating section, and
in a case in which the first communication section receives the read-out instructing information transmitted from the second communication section, the generating section starts reading-out of the charges accumulated in the charge storing sections.

9. The radiographic imaging system of claim 8, wherein
the control section transmits the read-out instructing information plural times and by wireless communication and even during a response wait time period, and
in a case in which the first communication section receives any of the read-out instructing information that are transmitted plural times from the second communication section, the generating section starts reading-out of the charges accumulated in the charge storing sections.

10. The radiographic imaging system of claim 8, wherein the control section transmits the read-out instructing information after standing-by for at least a predetermined irradiation standby time period from reception of the imaging start instructing information at the second communication section.

11. The radiographic imaging system of claim 8, wherein in a case in which the read-out instructing information is not received even if standing-by for a predetermined accumulating standby time period from transmission of the imaging start instructing information plural times, the generating section starts reading-out of the charges accumulated in the charge accumulating sections.

12. The radiographic imaging system of claim 1, wherein the radiographic imaging device further has a second notification section that gives notice in a case in which the first communication section receives predetermined instruction information relating to capturing of a radiographic image.

13. The radiographic imaging system of claim 12, wherein the predetermined instruction information is instruction information requesting capturing of a radiographic image.

14. The radiographic imaging system of claim 12, wherein the second notification section gives notice by using at least one of light and sound.

15. The radiographic imaging system of claim 12, wherein the second notification section is provided at a grasping portion for grasping at a time of carrying a main body of the radiographic imaging device.

16. A radiographic imaging device comprising:
a generating section that captures a radiographic image expressed by irradiated radiation, and generates image information expressing the captured radiographic image; and
a communication section that transmits, plural times and by wireless communication and even during a response wait time period, imaging start instructing information that instructs starting of imaging at a time when preparations for capturing a radiographic image by the generating section have been completed.

17. A control device comprising:
a communication section that is able to communicate with a radiographic imaging device that transmits, plural times and by wireless communication and even during a response wait time period, imaging start instructing information that instructs starting of imaging at a time when preparations for capturing a radiographic image have been completed; and
a control section that controls a radiation irradiating section such that radiation is irradiated with respect to the radiographic imaging device in a case in which any of the imaging start instructing information that are transmitted plural times is received from the communication section.

18. A radiographic imaging control method comprising:
transmitting, plural times and by wireless communication and even during a response wait time period, imaging start instructing information, that instructs starting of imaging at a time when preparations for capturing a radiographic image have been completed, from a radiographic imaging device that captures a radiographic image expressed by irradiated radiation and generates image information expressing the captured radiographic image; and
in a case in which any of the imaging start instructing information that are transmitted plural times from the radiographic imaging device is received at a control device that is able to communicate with the radiographic imaging device by wireless communication, controlling, by the control device, a radiation irradiating section such that radiation is irradiated with respect to the radiographic imaging device.

* * * * *